United States Patent [19]

Holtkamp

[11] Plant 4,875

[45] Aug. 10, 1982

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "OPTIMARA", Isselburg, Fed. Rep. of Germany

[21] Appl. No.: 172,124

[22] Filed: Jul. 25, 1980

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet known by the cultivar name Atlanta having light pink flower color, medium to dark green variegated leaves, with contrasting light green centers; upright and rigid stems; floriferous habit, with 7–12 flowers appearing on each stem, and uniform and compact growth habit.

1 Drawing Figure

The present invention comprises a new and distinct cultivar of African violet plant, botanically known as *Saintpaulia ionantha,* and hereinafter referred to by the cultivar name Atlanta.

The new cultivar was referred to during the breeding and selection process by the designation B 349/1, and is a product of a planned breeding program. The basic objective of the breeding program was to create a new African violet cultivar having very light pink flower color, a rich, full bouquet, and medium dark green leaves having light green centers. These are known in the industry as "girl-type" leaves.

The new cultivar was originated from a cross made in a controlled breeding program in Isselburg, West Germany. The female, or seed parent was a cultivar designated XIX34, pink girl. The male, or pollen parent was a cultivar designated XVII 148, a cultivar having apple blossom flower color.

The new cultivar Atlanta was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Atlanta has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Atlanta, which in combination distinguish this African violet as a new and distinct cultivar:

1. Variegated leaves, slightly serrated at the edges, and funnel-shaped.
2. The centers of the leaves are light green, in contrast to the darker green color surrounding the center.
3. Short, upright and rigid stems, 7–9 in number.
4. Very uniform growth and compact habit.

5. Very light pink flower color, and non-dropping flowers.
6. Highly floriferous, producing a full bouquet, with 7–12 flowers appearing on short wire-like peduncles on each stem.

The new cultivar is similar in certain respects to Nashville, disclosed in my U.S. Plant Pat. No. 4,533. Nashville similarly has "girl type" leaves. Atlanta is principally distinguished from Nashville by its flower color and flower petal form, with Nashville having ruffled edges.

The accompanying photographic drawing shows a typical specimen plant of the new cultivar. The colors appearing in the photograph are as true as possible with color illustrations of this type.

In the following description, color references are made to the Horticultural Color Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. cv. Atlanta.

Parentage:

*Male parent.*—XIX 34 pink girl.

*Female parent.*—XVII 148 apple blossom.

Propagation: The new cultivar holds its distinguishing characteristics through successive propagations by leaf cuttings and by division of shoots.

Plant: From 6 cm. to 8 cm. tall when grown in pots, and approximately 20–25 cm. in diameter when fully grown.

Leaves:

*General form.*—Round, wavy and funnel shaped.

*Diameter.*—Up to 60–70 mm.

*Texture.*—Soft, slightly hairy.

*Aspect.*—Firm, very shiny; younger leaves in center curly.

*Veins.*—Upperside barely visible; underside visible, light green.

*Color (upperside).*—Ivy green 0001060/1.

*Color (underside).*—Willow green 000862/2; light purple shade.

*Petiole.*—Color approximately sage green 000861/1.

Flowers:

*Buds.*—Bell-shaped; 6 mm. just before opening; 7–10 and more per stem.

*Sepals.*—Color: Greenish-brown. Calyx: Funnel-shaped. Aspect: Spear-shaped, hairy. Peduncle: Short, upright, wire-like, brownish, hairy.

Individual flowers:

*Size.*—Between 35–45 mm. in total diameter.

*Color.*—Upperside: Amaranth rose (3 larger petals) 530/3; 2 small petals 530/2; crystal-like. Underside: Amaranth rose 530/3.

*Borne.*—Flower stem carries 7–12 and more flowers on short strong peduncles; flowers occasionally display an additional small petal in the center of the flower.

*Shape.*—Normally conventional violet-shaped, but occasionally 3 large lower petals and 3 small upper petals.

*Flowering time.*—7–8 weeks after potting first flowers appear; 10–12 weeks to full-flowering saleable plant.

*Reproductive organs.*—Stamens: 2 anthers, composed of 4 cells, with seed capsule pushed slightly through. Anthers: Color Dresden yellow 64. Filaments: 5–7 mm. long; pinkish. Styles: 6–7 mm., pink-white stigma; base of ovary light green and hairy. Pollen color: HCC Dresden yellow 64/3.

*Roots.*—White when young and active; greenish brown where older; normally developed.

Disease resistance: Good, as experienced to date.

General observations: Atlanta is a compact growing variety with variegated shiny, funnel-shaped leaves with light green centers. The contrast between the medium to dark green leaves and the light pink flower head makes a very attractive plant.

I claim:

1. A new and distinct cultivar of African violet known by the cultivar name Atlanta, as described and illustrated, and particularly characterized by its light pink flower color, medium to dark green variegated leaves, with contrasting light green centers; upright and rigid stems; floriferous habit, with 7–12 flowers appearing on each stem, and by its uniform and compact growth habit.

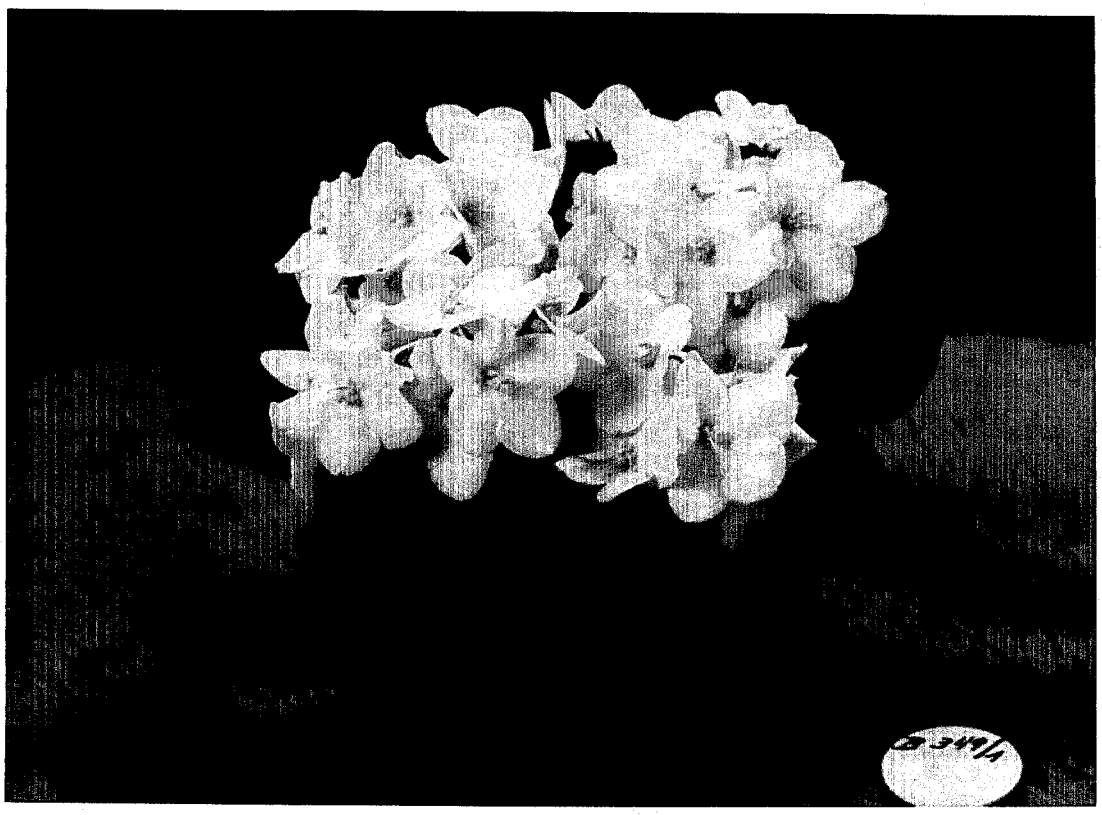

* * * * *